(12) United States Patent
Simmons

(10) Patent No.: US 7,914,483 B2
(45) Date of Patent: Mar. 29, 2011

(54) PAIN CONTROLLED ANALGESIC ("PCA") APPARATUS

(75) Inventor: Mark Randal Simmons, Grayslake, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 12/061,496

(22) Filed: Apr. 2, 2008

(65) Prior Publication Data
US 2009/0254025 A1 Oct. 8, 2009

(51) Int. Cl.
*A61M 31/00* (2006.01)
(52) U.S. Cl. .......................................................... 604/67
(58) Field of Classification Search .................. None
See application file for complete search history.

(56) References Cited

U.S. PATENT DOCUMENTS

| | | |
|---|---|---|
| 5,041,086 A | 8/1991 | Koenig et al. |
| 5,860,957 A | 1/1999 | Jacobsen et al. |
| 5,957,885 A | 9/1999 | Bollish et al. |
| 6,010,483 A | 1/2000 | Spencer |
| 6,135,949 A | 10/2000 | Russo et al. |
| 6,231,560 B1 | 5/2001 | Bui et al. |
| 6,241,704 B1 | 6/2001 | Peterson et al. |
| 6,290,681 B1 | 9/2001 | Brown |
| 6,567,001 B1 * | 5/2003 | Barrieau et al. ............... 340/506 |
| 6,577,899 B2 | 6/2003 | Lebel et al. |
| 6,807,965 B1 | 10/2004 | Hickle |
| 6,929,619 B2 | 8/2005 | Fago et al. |
| 7,025,743 B2 | 4/2006 | Mann et al. |
| 7,144,384 B2 | 12/2006 | Gorman et al. |
| 2002/0017296 A1 * | 2/2002 | Hickle ...................... 128/203.12 |
| 2005/0102167 A1 | 5/2005 | Kapoor |
| 2005/0273056 A1 | 12/2005 | Haury et al. |

OTHER PUBLICATIONS

ECRI: "Patient-controlled analgesic infusion pumps," Health Devices, Jan. 1, 2006, pp. 5-35.
International Search Report and Written Opinion for International Application No. PCT/US2009/038725 mailed on Aug. 11, 2009.

* cited by examiner

*Primary Examiner* — Nicholas D Lucchesi
*Assistant Examiner* — Pritesh Patel
(74) *Attorney, Agent, or Firm* — K&L Gates LLP

(57) ABSTRACT

An infusion pump includes: a housing, a pump actuator supported by the housing, electronics configured to control the pump actuator, a pain controlled analgesic ("PCA") input device, a cord having a remote end connected to the PCA input device and a local end connected to the housing, a remote integrated circuit; and a local integrated circuit in communication with the electronics and the remote integrated circuit so as to provide operational information concerning the PCA input device to the electronics.

35 Claims, 5 Drawing Sheets

FIG. 6

|  | Signal Processing Scenario #1 | Signal Processing Scenario #2 | Signal Processing Scenario #3 |
|---|---|---|---|
| Signal Generation | Remote IC Local IC | Local IC Remote IC | Remote IC Local IC |
| Data Manipulation | Actuator Proc/Mem | Remote IC | Local IC |
| Pump Activation Alert Generation | Actuator Proc/Mem | Actuator Proc/Mem | Actuator Proc/Mem |

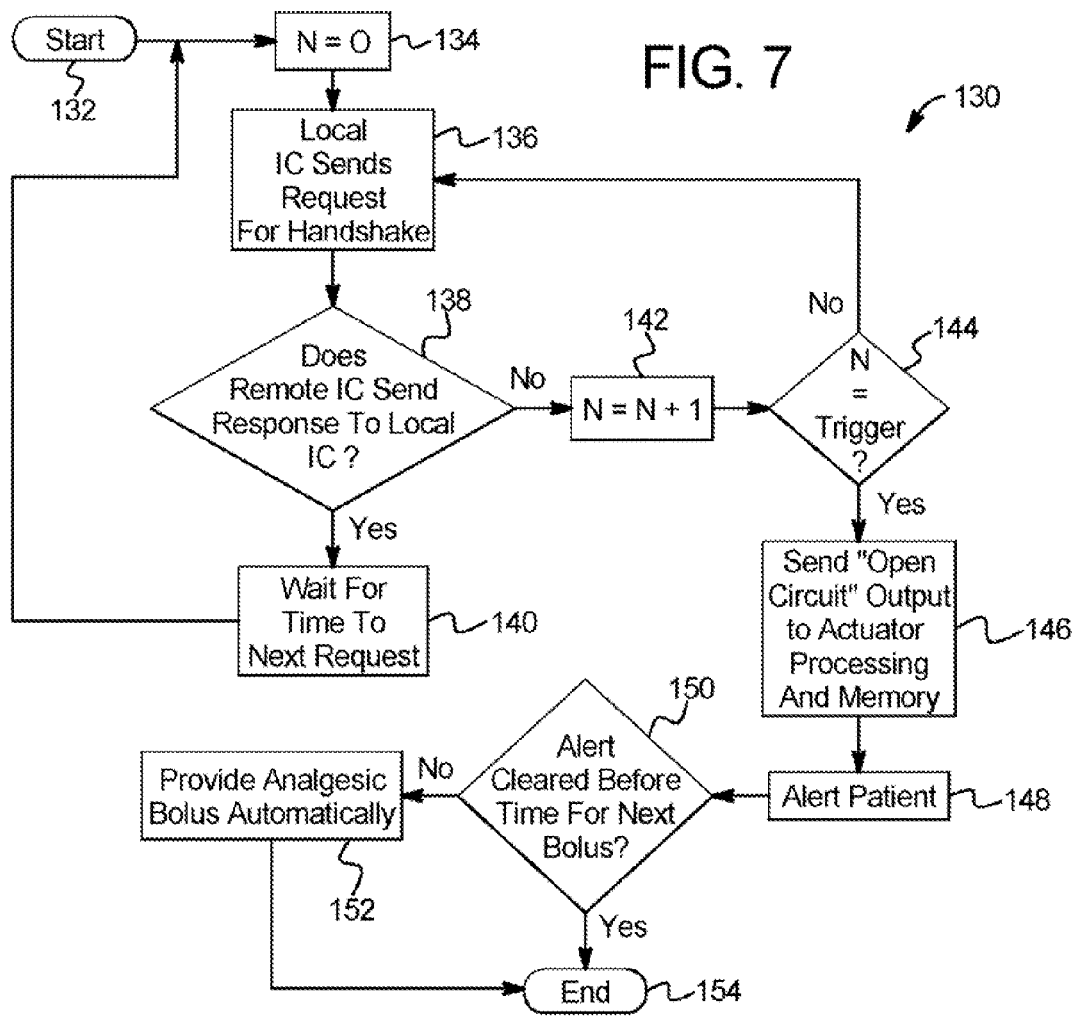
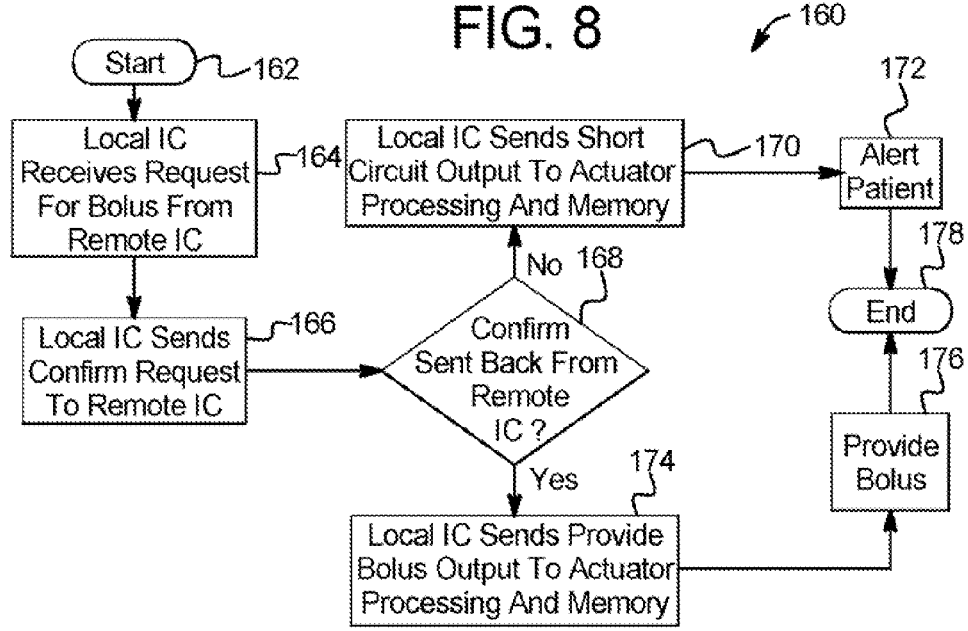

PAIN CONTROLLED ANALGESIC ("PCA") APPARATUS

BACKGROUND

The present disclosure relates to medication delivery and more particularly to delivery of a pain controlled analgesic ("PCA").

Infusion pumps are used to administer liquid drugs to patients. The liquid drug is supplied from a source of the drug and delivered to the patient via a catheter or other injection device. The infusion pump controls the manner in which the liquid drug is infused to the patient. The pump can have various modes of infusion. An infusion pump can operate in different modes of infusion, such as: (i) a continuous mode in which the pump delivers a single volume at a single rate; (ii) an auto-ramp mode in which the pump delivers the liquid drug at a rate that gradually increases to a threshold rate, remains at the threshold rate for a period of time, and then gradually decreases; (iii) an intermittent mode in which the pump delivers discrete liquid volumes spaced over relatively long periods of time, such as a liquid volume every three hours; (iv) a custom mode in which the pump can be programmed to deliver a unique infusion rate at discrete time periods; and (v) a pain controlled analgesic ("PCA") mode during which the pump periodically infuses boluses of an analgesic in response to requests by the patient.

The PCA delivery has a number of benefits including: (i) a time savings between when the patient feels pain and/or the need to receive analgesia and when the drug is administered; (ii) a reduction of workload of the nursing staff (an amount of the prescribed analgesic, enough for multiple doses, is preloaded into the infusion device and delivered via PCA mode); (iii) reduction of the chance for medication error (PCA programmed per physician's order for amount); (iv) patients receive medicine when they need it, instead of having to wait for the nursing staff; (v) patients who use PCA devices have reported better analgesia and lower pain scores than those patients who have to request analgesia from the nursing staff; and (vi) PCA provides a measurement of how much pain an individual patient is experiencing from one day to the next.

PCA modes of drug delivery involve the intravenous, epidural, or subcutaneous administration of a liquid opioid. The infusion pumps currently in use for PCA in some instances give the clinician two parameters to set when prescribing a given drug for a patient: (i) a dose or bolus amount of drug administered whenever the patient presses a button and (ii) a lockout interval which determines how soon after a bolus is administered that a second bolus can be delivered if the patient presses the button again. If a patient presses the button before the lockout interval has elapsed, the PCA pump ignores the request. The dose and lockout are programmed into the pump for an individual patient and drug combination. The dose is prescribed based on the clinician's assessment of the patient's drug or opioid requirement (depending on weight and habituation. The lockout interval is generally set depending on the time to onset of clinical effect of a given drug. The lockout interval is used to prevent a patient drug overdose resulting from giving himself or herself another bolus before the previous bolus has had a chance to take effect.

Sometimes a third parameter is programmed into a pump providing PCA. This is the flow rate of a continuous infusion of medication providing a background of opioid on top of which PCA is added. The continuous infusion is adjusted to provide the minimum amount of drug needed by a patient over time. The PCA component then allows the patient to administer extra (rescue or break-through-pain) doses as needed. This technique of using a continuous infusion along with PCA minimizes the requirement for a patient to push the button repeatedly as a bolus wears off. This is particularly useful at night when the patient's sleep would otherwise be interrupted regularly.

The PCA button is connected to the infusion pump via a cord. The infusion pump supplies an analog voltage to the button. The infusion pump's electronics recognizes a patient's closure of the PCA button by detecting a change in voltage level, which is normally not seen but seen when the button is pressed.

The analog cables can be prone to a number of errors. A frayed wire or wires within the cord may not allow current to flow or enough current to flow to trigger the electronics when the patient pushes the PCA button, rendering the pump unable to deliver a bolus of analgesic, or possibly delivering a bolus when it is not needed or has not been requested. Or, the wires can become short circuited, damaging electrical components in the pump or opening a fuse, which may need to be replaced, and may also lead to improper analgesic dosage delivery.

A need accordingly exists for an improved PCA input apparatus and method.

SUMMARY

The present disclosure provides a pain controlled analgesic ("PCA") apparatus, which is more reliable than current systems.

In one embodiment, an infusion pump is provided that is connected to a PCA input device having one or more button. The device is connected to the pump's primary housing via a cord. The PCA input device includes a remote microchip or integrated circuit. The chip or circuit communicates with a local chip or circuit located at the infusion pump. Communication between the remote (button) microchip and local (pump) microchip is performed digitally and/or through frequency matching. Communication protocols such as Inter-Integrated Circuit ("I²C"), Serial Peripheral Interface Bus ("SPI") (two or three wire), Transistor-Transistor Logic Universal Asynchronous Receiver/Transmitter ("TTL UART"), or Standard RS232 Universal Asynchronous Receiver/Transmitter ("RS232 UART") may be used between the remote and local microchips. The type of protocol chosen depends upon the number of wires in the cord. The cord can have, for example, a single fiber optic cable, two wires or three wires, which are configured to carry low analog voltage, e.g., 3 to 24 VDC, signals.

The remote microchip senses when the one or more PCA button is pressed and sends a corresponding signal to the local microchip. The local microchip in turn is connected electrically to the pump's processing and memory, which causes a pump motor to deliver a bolus of analgesic if conditions are appropriate to do so, e.g., if the current button press has not occurred too soon after previous button press.

The digital protocol (digital message protocol or frequency waveform) is configured to sense for example when a communication line has been broken, e.g., through the lack of response from a handshaking request from the local microchip to the remote microchip. For example, the local microchip can be programmed to send a handshake request to the remote microchip after a predetermined time interval. If the request is sent and no response is sent back, the local microchip can tell the pump processing and memory that there is a problem with the PCA button. The local microchip can either be programmed to send a second handshake request or be told to do so by the pump electronics. If a second handshake request is again not answered (second attempt not absolutely necessary or more than one second request could be made) the infusion pump is configured to take appropriate action.

In one embodiment, appropriate action includes providing an alarm or alert at the pump, e.g., in the form of an audible alarm and a message on the pump's video screen saying, e.g., "PCA disabled." Alternatively or additionally, the pump can be configured to provide a dose of analgesic to the patient either at a preset interval and dose or at a last recorded interval and dose. For example, if the alarm is not cleared, e.g., no nurse has responded or the patient is at home and asleep, and a period of time transpires after which the pump should have been told to deliver a dose of analgesic, the pump can provide a dose, e.g., prescribed dose of the analgesic and continue to do so at the set intervals until the alarm is cleared.

The above handshaking routine is performed regularly enough in one embodiment such that a broken or frayed cord is detected before the patient is likely to press the PCA button. Either the remote or local microchip or the pump electronics can be programmed to look for other PCA input failures, such as failures with the PCA button or switches within the input device housing the button. To this end, any one or more of the microchips and the pump electronics can have programmable processing and memory to detect additional failure modes.

For example, the button of the PCA input device is a momentary button in one embodiment, which the patient need only press for a moment to initiate delivery of an analgesic bolus. When the patient releases the button, a spring pushes the button such that a break in electrical contact is made. It may happen that the spring does not function properly and the button stays depressed after the patient releases the button. In such a case, the PCA system of the present disclosure can detect the stuck button in a myriad of ways.

In one way, the remote integrated circuit detects a constant rather than a momentary input from the PCA button. The remote integrated circuit has programmed processing and memory to determine a stuck button condition, the remote integrated circuit sends a "stuck button" message to the local integrated circuit, which relays the message to the pump's processing and memory, which alarms and takes other corrective action.

In another way, the remote integrated circuit detects a constant rather than a momentary input from the PCA button and relays the constant signal to the local integrated circuit. The local integrated circuit has programmed processing and memory to determine a stuck button condition, the local integrated circuit sends a "stuck button" message to the pump's processing and memory, which alarms and takes other corrective action.

In a further way, the remote integrated circuit detects a constant rather than a momentary input from the PCA button and relays the constant signal to the local integrated circuit, which in turn relays the signal to the pump's processing and memory. The pump's processing and memory has programmed processing and memory to determine a stuck button condition and alarms and takes other corrective action.

In another example, the button of the PCA input device is a maintained button, which the patient need only press for a moment to initiate delivery of an analgesic bolus. When the patient releases the button in this instance, however, the button remains depressed until another action causes the button to release, e.g., a timer times out or the bolus is competed. Here, the mechanism holding the button in a depressed state, e.g., against a spring, may have trouble maintaining electrical contact, causing the button to intermittently make contact or "chatter." In this case too, the PCA system of the present disclosure can detect the chattering PCA contact in a myriad of ways by placing the programmed processing an memory at the remote integrated circuit, the local integrated circuit or the pump's processing and memory as described above for the stuck PCA button.

In a further example, the wires within the PCA cord can become shorted causing a false request for a bolus dose. Here, a continuous signal can be treated the same as a stuck button by placing the programmed processing and memory at either the local integrated circuit or the pump's processing an memory. Alternatively, when the local integrated circuit receives a signal from the remote integrated circuit requesting an analgesic bolus, the local integrated circuit can send a handshake signal back to the remote integrated circuit for the remote integrated circuit to confirm. The remote integrated circuit will either not send the confirm signal or the shorted lines will impede the signal.

It is accordingly an advantage of the present disclosure to provide an improved infusion pump.

It is another advantage of the present disclosure to provide an infusion pump having an improved pain controlled analgesic ("PCA") input device.

It is a further advantage of the present disclosure to provide a PCA input device having diagnostic capability for both the input device and the cord connecting the input device to the pump housing.

It is yet another advantage of the present disclosure to provide a PCA input device having open circuit detection capability.

It is yet a further advantage of the present disclosure to provide a PCA input device having short circuit detection capability.

It is still another advantage of the present disclosure to provide a PCA input device having button stuck detection capability.

It is still a further advantage of the present disclosure to provide a PCA input device having button chatter detection capability.

Further still, it is an advantage of the present disclosure to provide an infusion pump having a PCA input system that can detect when the PCA input device is not functioning properly and override the PCA input device and provide an analgesic dose automatically.

Additional features and advantages are described herein, and will be apparent from, the following Detailed Description and the figures.

BRIEF DESCRIPTION OF THE FIGURES

FIG. 6 is a chart showing different embodiments for communication between the integrated circuits and pump control of the present disclosure.

FIG. 7 is a logic flow diagram illustrating one frayed cord or open circuit method of operation for the PCA apparatus of the present disclosure.

FIG. 8 is a logic flow diagram illustrating one crossed-wire or short circuit method of operation for the PCA apparatus of the present disclosure.

DETAILED DESCRIPTION

Figure 1:
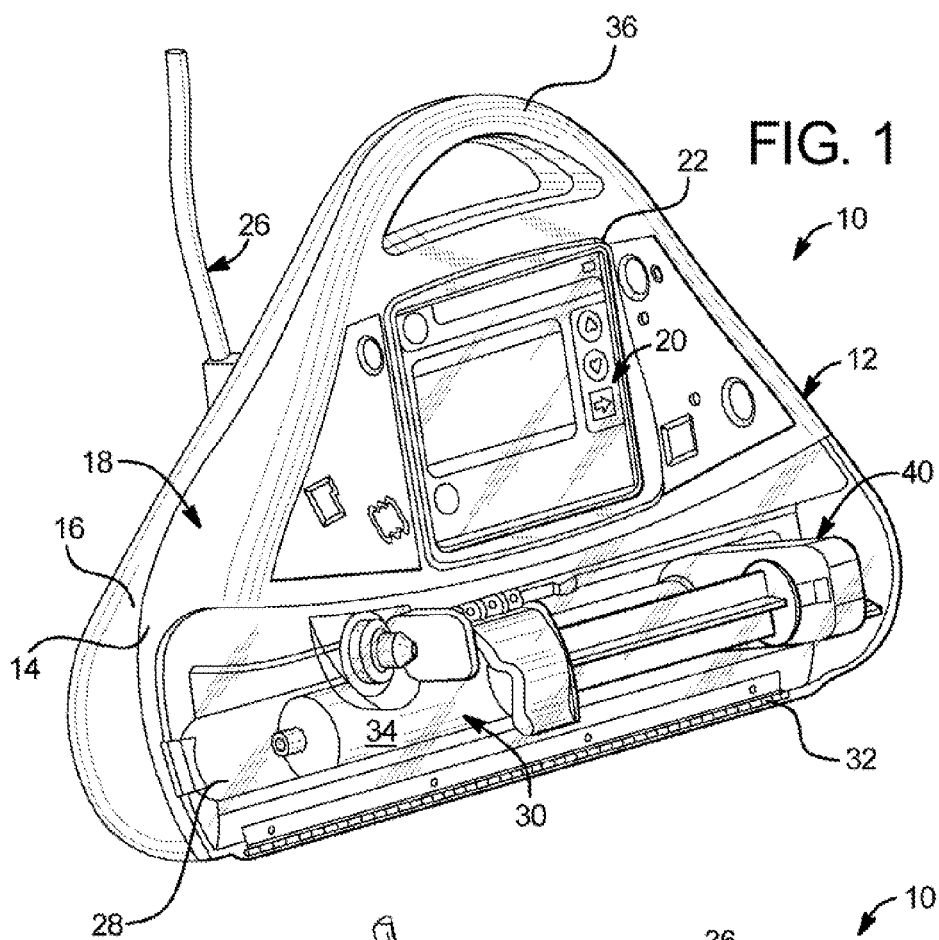
FIG. 1 is a perspective view illustrating one embodiment of an infusion pump of the present disclosure.
Figure 2:
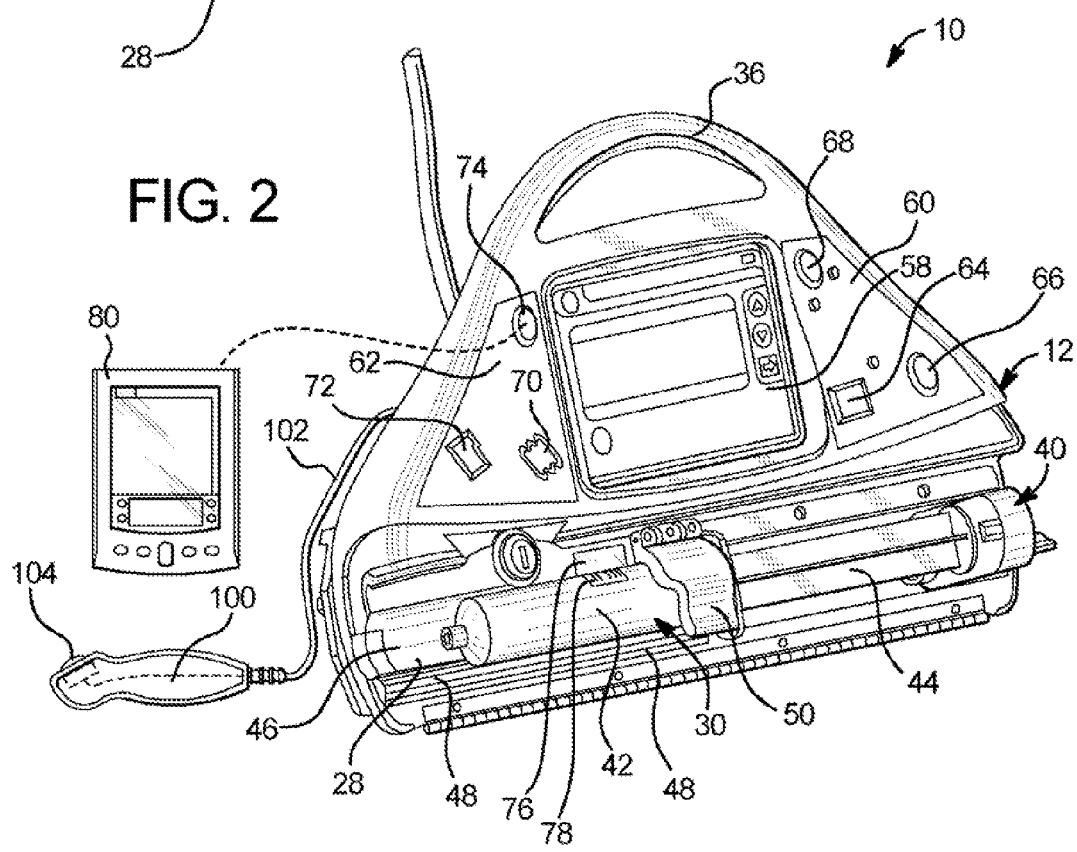
FIG. 2 is another perspective view illustrating one embodiment of an infusion pump of the present disclosure.

Referring now to the drawings and in particular to FIGS. 1 and 2, an embodiment of an infusion pump 10 having the microchip based pain controlled analgesic ("PCA") apparatus of the present disclosure is illustrated. Infusion pump 10 includes a housing 12. In the illustrated embodiment, housing 12 of infusion pump 10 has a generally contoured shape. Housing 12 can have other shapes if desired.

The housing 12 includes a first member 14 and a second member 16 that are connected together to form a central cavity 18. Central cavity 18 houses various components of the pump 10 including the user interface 20. The first member 14 of the housing has an opening 22 that accommodates a display screen of the user interface 20. A rear portion of the housing 12 has a receptacle or recess 24 that is adapted to receive a power supply 26. At a bottom, front portion of the housing 12, a container compartment or syringe compartment 28 is defined that accommodates a syringe assembly 30, a portion of a drive mechanism 40 and other components. The first member 14 of the housing 12 has a hinged access door 32 that encloses syringe assembly 30 in compartment 28. Access door 32 can be transparent for medical personnel to view the contents within syringe assembly 30.

A lock 34 is provided with door 32 to prevent unauthorized access to syringe assembly 30. An upper portion of the housing 12 is provided with a handle 36. Housing 12 can be made from a variety of materials including various types of plastics and metals. Housing 12 has a pole clamp 38 attached to the second member 16 of the housing 12. Pole clamp 38 can have various designs and is adapted to mount pump 10 on a pole assembly used in a hospital setting. In one embodiment, pole clamp 38 can mount pump 10 in various positions. For example, the pump 10 can be mounted in a generally horizontal position shown in FIGS. 3A and 3B of U.S. Pat. No. 7,018,361 ("the '361 patent") entitled "Infusion Pump", the entire contents of which are incorporated herein by reference.

FIG. 2 shows syringe compartment 28 in greater detail. Syringe compartment 28 is dimensioned to receive and support the syringe assembly 30 and receive a portion of drive mechanism 40. Syringe assembly 30 includes a syringe barrel 42 and a syringe plunger 44. Syringe barrel 42 contains medication and slidably receives the syringe plunger 44. Drive mechanism 40 drives syringe plunger 44 to force medication from the syringe barrel 42 through a tube (not shown) and to a patient. The tube has one end connected to an end of the syringe barrel 42 and another end configured to be connected to a patient.

The syringe compartment 28 has a rear wall 46 that is generally concave to receive the syringe barrel 42 of the syringe assembly 30. The syringe barrel 42 of the syringe assembly 30 and rear wall 46 are generally in confronting relation. The housing 12 further has a curved lip 48 that in one embodiment is integral with the rear wall 46. Lip 48 aids in loading a syringe 26 in the compartment 28 to be described in greater detail below. As shown in FIG. 2, a syringe clamp 50 is movably mounted in the compartment 28. The clamp 50 has a concave inner surface that faces the rear wall 46 and that fits over the syringe barrel 42. Clamp 50 is slidable along a rod assembly (see number 54 at FIG. 18 of the '361 patent) to move the clamp 50 towards and away from the rear wall 46. The clamp 50 can slide along the rod assembly 52 to accommodate different sized syringe barrels. A base portion of the clamp 50 has a pair of rollers 54, 56 that help reduce friction when the clamp 50 slides along the housing 12. Due to tolerances, the clamp 50 may also pivot slightly. Clamp 50 is resiliently biased towards rear wall 46.

Housing 12 and syringe compartment 28 are sized such that an entire syringe assembly, with plunger fully extended from the syringe barrel, is contained within the housing and can be enclosed by the access door 32. No part of a syringe barrel or syringe plunger protrudes from the housing 12. A portion of the drive mechanism 40 extends into the syringe compartment 28 to engage the plunger 44. Access door 32 has an opening that accommodates the tube (not shown) that is attached to the syringe barrel 42 to deliver medication to the patient.

As shown in FIG. 1, pump 10 has a user interface 20. Portions of the user interface 20 are described in greater detail in commonly owned U.S. patent application Ser. No. 10/172, 808 (2004-0225252) entitled "System And Method For Operating An Infusion Pump", the entire contents of which are incorporated herein by reference. User interface 20 includes a display screen 58, a first control panel 60, a second control panel 62 and associated electrical components and computer software contained within the housing 12 to operate the pump 10. Display screen 58 displays all of the general operating parameters of the pump 10 and fits within the opening 22 in the housing 12.

The display screen 58 in one embodiment operates with a touch screen overlay for a user to enter data to be into the pump 10. As discussed, the pump 10 can be mounted in either a generally horizontal position or a generally vertical position. The software associated with the user interface 20 and pump 10 has the ability to display information on the screen 58 in either a landscape orientation or a portrait orientation. When the pump is mounted in the horizontal configuration information is displayed on the display screen 50 in a landscape configuration. When pump 10 is mounted in the vertical configuration, information is displayed on the display screen 50 in a portrait configuration. Thus, depending on how the pump 10 is mounted, the information can be read by users without the need to tilt one's head. This feature is described in greater detail in commonly-owned U.S. Pat. No. 6,997,905 entitled "Dual-Orientation Display For Medical Devices", the entire contents of which are incorporated herein expressly by reference. First control panel 60 has a start button 64, a stop button 66 and an alarm/alert button 68. Second control panel 62 has a settings panel 70, a history button 72 and a data port 74. Pump 10 also includes a radio frequency identification ("RFID") reader 76, which reads a radio frequency ("RFID") tag 78 placed on syringe barrel 42. Data port 74 in one embodiment is an infrared data port, which communicates with a personal data assistant ("PDA") 80 operated by a nurse or clinician.

The pump 10 provides patient-controlled analgesia ("PCA"). As shown in FIG. 2, pump 10 includes a PCA input device 100, which allows the patient to manually actuate the pump actuator to deliver a bolus of analgesic to the patient when desired and when proper. PCA input device 100 is connected via a cord 102, which is plugged into or otherwise connected to housing 12 of pump 10. PCA input device 100 in one embodiment includes a peripheral structure that protects against inadvertent actuation. The PCA input device 100 and/ or cord 102 can also be lighted so as so glow in the dark to aid patients in locating the button. PCA input device 100 includes a button 104, which can be a momentary or maintained button as discussed in detail below.

Figure 3:
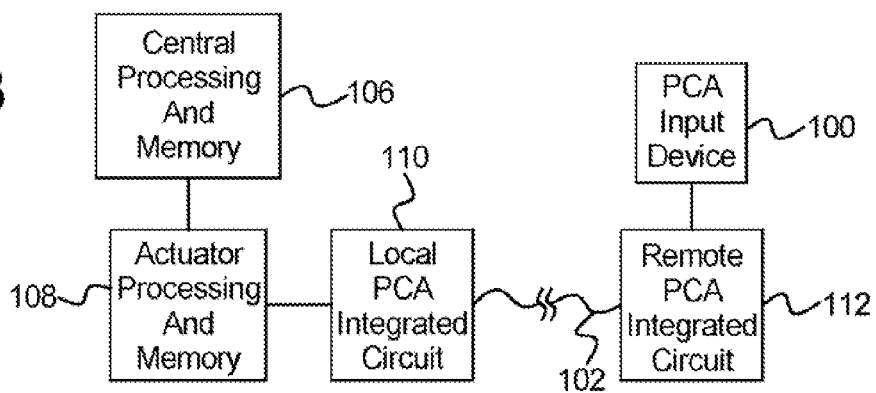
FIG. 3 is a schematic view showing one embodiment of a control architecture for the pain controlled analgesia ("PCA") apparatus of the present disclosure.

Referring now to FIG. 3, one embodiment for an electrical layout for pump 10 as it relates to PCA input device 100 is illustrated. Pump 10 includes a plurality of processors, which can be a master processor (e.g., a central processing unit) running a plurality of delegate processors. Pump 10 can also include a safety processor to provide redundancy and ensure proper operation of the other processors. Central processing and memory 106 in one embodiment oversees the pump actuator processing and memory 108, which in turn controls the movement of drive mechanism 40 that drives syringe plunger 44 to force medication from the syringe barrel 42 through the syringe plunger.

It should be appreciated that while a syringe pump is illustrated, pump 10 can be a peristaltic pump, a micro-pump, a piezoelectric pump, each capable of delivering a medical fluid to a patient. Accordingly, while the source of the drug or medicament is shown as being syringe barrel 42, the source is alternatively a bag or other medical fluid container. Still further alternatively, pump actuator processing and memory 108 in an alternative embodiment are integrated with central processing and memory 106.

Pump actuator processing and memory 108 likewise communicates with a local PCA controller 110. Communication between actuator processing and memory 108 and local PCA controller 110 can be via a protocol, such as Inter-Integrated Circuit ("I²C"), Serial Peripheral Interface Bus ("SPI") (two or three wire), Transistor-Transistor Logic Universal Asynchronous Receiver/Transmitter ("TTL UART") and Recommended Standard 232 Universal Asynchronous Receiver/Transmitter ("RS232 UART"). In a similar manner, local PCA controller 110 can communicate with remote controller 112 via a protocol, such as Inter-Integrated Circuit ("I²C"), Serial Peripheral Interface Bus ("SPI") (two or three wire), Transistor-Transistor Logic Universal Asynchronous Receiver/Transmitter ("TTL UART"), Recommended Standard 232 Universal Asynchronous Receiver/Transmitter ("RS232 UART") and fiber optic cable. As seen in FIG. 3, local PCA controller 110 is separated from remote PCA controller 112 via cord 102. The signals between controllers 110 and 112 can be low voltage analog, e.g., zero to five VDC or 4 to 20 milliamp, signals.

Remote controller 112 operates with PCA input device 100 to receive an input from the patient when the patient presses button 104 to receive a bolus of analgesic. When button 104 of PCA input device 100 is pressed, remote integrated circuit or microchip 112 sends a digital message to local integrated circuit or microchip 110. As shown below, local integrated circuit or microchip 110 can also send a digital message to remote integrated circuit or microchip 112 either by way of response or to initiate a handshake or other desired back-and-forth with remote integrated circuit or microchip 112. Remote integrated circuit or microchip 112 can also respond to a digital message sent from local integrated circuit or microchip 110.

Figure 4:
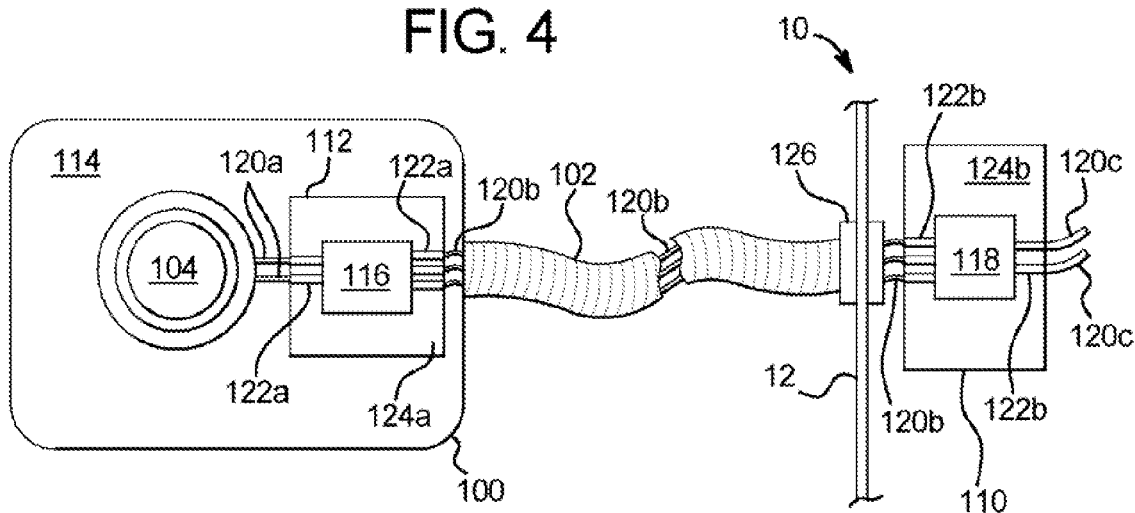
FIG. 4 is a schematic view illustrating one embodiment for configuring the integrated circuits disclosed herein with the PCA apparatus of the present disclosure.
Figure 5:
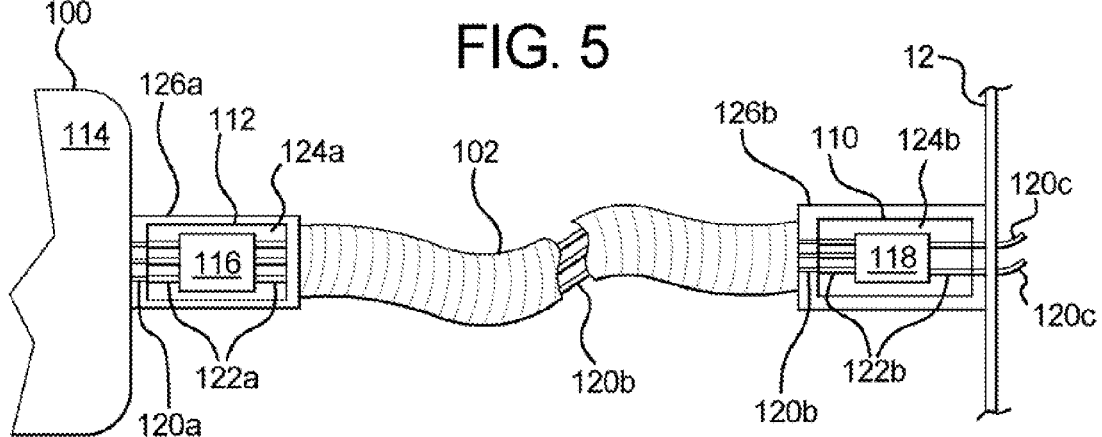
FIG. 5 is a schematic view illustrating another embodiment for configuring the integrated circuits disclosed herein with the PCA apparatus of the present disclosure.

Referring now to FIGS. 4 and 5, two different configurations for the remote and local controllers 110 and 112, relative to PCA cable 102, PCA input device 100 and housing 12 of pump 10 are illustrated. FIG. 4 illustrates one embodiment in which local integrated PCA circuit 110 is housed within housing 12 of pump 10 and remote integrated PCA circuit 112 is located within a housing 114 of PCA input device 100. Remote controller 112 can include at least one integrated circuit chip or microchip 116, such as an off the shelf, low power utilization, electronic microchip. Remote controller 112 is shown connected to button 104 via wires 120a. Alternately, button 104 includes a contact that mates with a contact located directly on remote controller 112, making separate wires unnecessary. Remote controller 112 is also connected electrically to wires 120b of cord 102. Wires 120a and 120b connect to microchip 116. Microchip in one embodiment includes onboard processing and memory. However, processing and memory external to microchip 116 could be used alternatively. Traces 122a formed on a printed circuit board ("PCB") 124a connect microchip 116 to wires 120a and 120b and associated downstream components.

Cord 102 is connected to housing 12 of pump 10 via an electrical fitting 126. Local controller 110 can include at least one off of the shelf integrated circuit chip or microchip 118, which also has onboard processing and memory (processing and memory are alternatively external). Local controller 110 is connected electrically to wires 120b of cord 102. Wires 120c connect local controller 110 to actuator processing and memory 108 (FIG. 3). Wires 120b and 120c connect to microchip 118 via traces 122b formed on a PCB 124b, to which microchip 118 is also soldered. Local controller 110 is located alternatively on a same PCB as actuator processing and memory 108 (FIG. 3) and communicates with actuator processing and memory 108 via circuit board traces. Cord 102 in the illustrated embodiment is a three-wire cord but alternatively has a different number of wires 120b if needed.

In the alternative embodiment of FIG. 5, cord 102 incorporates local controller 110 and remote controller 112 into connectors 126a and 126b of the cord, which in turn connect cord 102 respectively to PCA device 100 and pump 10. Remote controller 112 of connector 126a of FIG. 5 can include at least one integrated circuit chip or microchip 116. Remote controller 112 is shown connected to button 104 via wires 120a. Remote controller 112 is also connected electrically to wires 120b of cord 102. Wires 120a and 120b connect to microchip 116 via traces 122a formed on a printed circuit board ("PCB") 124a to which microchip 116 is soldered.

Local controller 110 of connector 126b of FIG. 5 can include at least one integrated circuit chip or microchip 118. Local controller 110 is connected electrically to wires 120b of cord 102. Wires 120c connect local controller 110 to actuator processing and memory 108 (FIG. 3). Wires 120b and 120c connect to microchip 118 via traces 122b formed on a PCB 124b to which microchip 118 is soldered.

FIG. 6 illustrates, without limitation, three processing scenarios for local controller 110 and remote controller 112. Three functions separating the three processing scenarios include (i) signal processing, (ii) data manipulation, and (iii) pump actuation and alert generation. In the first scenario, local controller 110 and remote controller 112 are both configured to pass signals to each other. Local controller 110 is configured to send and receive signals from actuator processing and memory 108 (FIG. 3).

In the first scenario, local controller 110 and remote controller 112 do not perform any data manipulation such as add, subtract and/or manipulate the data as set forth below in the algorithms of FIGS. 7 to 10. Here, actuator processing and memory 108 performs the above-mentioned data manipulation and controls the pump to deliver an analgesic bolus or causes an alert to be sounded, whichever is needed. Here, remote controller 112 senses an input, e.g., press of button 104, sends a corresponding signal to local controller 110, which relays the signal to actuator processing and memory 108, which in turn controls the pump to deliver an analgesic bolus or causes an alert to be sounded, whichever is needed.

In the second scenario, local controller 110 and remote controller 112 are both configured to pass signals to each other. Local controller 110 is configured to send and receive signals from actuator processing and memory 108 (FIG. 3). In the second scenario, remote controller 112 is configured to perform data manipulation such as add, subtract and/or manipulate the data as set forth below in the algorithms of FIGS. 7 to 10. Here, remote controller 112 senses an input, e.g., press of button 104, remote controller 112 manipulates data to determine when an alarm needs to be generated or the pump is to be actuated. Remote controller 112 sends a corresponding signal to local controller 110, which relays the signal to actuator processing and memory 108, which in turn controls the pump to deliver an analgesic bolus or causes an alert to be sounded, whichever is needed.

In the third scenario, local controller 110 and remote controller 112 are both configured to pass signals to each other. Local controller 110 is configured to send and receive signals from actuator processing and memory 108 (FIG. 3). In the second scenario, local controller 110 is configured to perform data manipulation such as add, subtract and/or manipulate the data as set forth below in the algorithms of FIGS. 7 to 10. Here, remote controller 112 senses an input, e.g., press of button 104, and sends a corresponding signal to local controller 110. Local controller 110 manipulates data to determine when an alarm needs to be generated or the pump is to be actuated. Local controller 110 sends a corresponding signal to actuator processing and memory 108, which in turn controls the pump to deliver an analgesic bolus or causes an alert to be sounded, whichever is needed.

Referring now to FIG. 7, an algorithm 130 stored at any of local controller 110, remote controller 112 and actuator processing and memory 108 illustrates one embodiment in which the PCA system of the present disclosure is configured to determine when cord 102 has become frayed. Upon starting at oval 132, algorithm 130 sets a counter N=0. Local controller 110 is configured to send periodically, e.g., every half-minute, minute or multiple of a minute, a handshake request to remote controller 112, as seen at block 136. If remote controller 112 sends a response to the handshake request to local integrated circuit, meaning proper communication exists between the two controllers (cord is not frayed), as determined at diamond 138, algorithm 130 waits for the next time to send a handshake request, as seen at block 140, sets N again to zero, and sends another request at block 136. The loop between blocks 134 and 136, diamond 138 and block 140 continues until a handshake response is not sent, as determined at diamond 138.

It should be appreciated that if cord 102 becomes frayed right after the handshake response is sent and the patient at that second presses button 104 for a bolus of analgesic, algorithm 130 will do nothing until the timer times out at block 140. Although the scenario above is unlikely, it is still desirable to make the time to next request at block 140 relatively small. This way, when cord 102 becomes frayed, only a few seconds or a minute has to pass before such fray is detected. It should also be appreciated that the handshake request can be sent instead from remote controller 112 to local controller 110, which sends the handshake response back to remote controller 112. Algorithm 130 will operate equally as well.

When a handshake response is not sent, as determined at diamond 138, algorithm 130 advances a counter to N=N+1, as seen at block 142. The counter serves as a double, triple or multiple check that the cord is actually frayed. Determining if N=trigger amount at diamond 144 provides a redundant check. Setting N=3 at diamond 144 for example looks to see if handshake is missing over three cycles and so on. If N is not yet equal to the set trigger amount as determined at diamond 144, algorithm 130 is configured to send another handshake request at block 136. If a handshake response is now sent as determined at diamond 138 the count is cleared back to zero at block 134. If a handshake response is again not sent as determined at diamond 138, N is increased again at block 142.

When N reaches the trigger amount at diamond 144, algorithm 130 assumes that cord 102 has become frayed, severed or otherwise inoperable. At block 146, an "open circuit" alert is sent to actuator processing and memory 108. It should be appreciated that the counting feature could be left out of algorithm 130, so that an open circuit is determined after a first time there is no response to a handshake request. Actuator processing and memory 108 provides an audio, visual or audiovisual alert at pump 10, a remote location or both asking the patient or clinician to check cord 102, as seen at block 148.

Another optional feature is shown at diamond 150. Pump 10 in one embodiment records the time between the last two analgesic bolus deliveries. Thus pump 10 knows when the next analgesic bolus is likely to be requested. Pump 10 in one embodiment provides an automatic bolus after the last recorded period of time passes, after the last recorded period of time plus an additional time amount passes, or after a predetermined period of time passes. In algorithm 130, if the alert or alarm is cleared before the next bolus time occurs, as determined at diamond 150, it is assumed that the frayed cord 102 has been swapped out or that the patient otherwise has an avenue to receiving an analgesic bolus, and algorithm 130 ends as seen at oval 154. In algorithm 130, if the alert or alarm is not cleared before the next bolus time occurs, as determined at diamond 150, a bolus of analgesic is provided automatically to the patient as seen at block 152, after which algorithm 130 ends as seen at oval 154.

Referring now to FIG. 8, an algorithm 160 stored at any of local controller 110, remote controller 112 and actuator processing and memory 108 illustrates one embodiment in which the PCA system of the present disclosure is configured to determine when cord 102 has a short circuit, e.g., insulation on wires 120b is missing so that two wires become conducting. Algorithm 160 starts at oval 162 when it is assumed that the patient has pressed bolus button 104 to request a bolus of analgesic. A corresponding signal is sent from remote controller 112 to local controller 110, as seen at block 164. At block 166 local controller 110 sends a confirm request signal to remote controller 112.

If a confirm signal is not sent back from remote controller 112 to local controller 110, as determined at diamond 168, the local integrated circuit sends a "short circuit" signal or output to actuator processing an memory 108, as seen at block 170, which provides an audio, visual or audiovisual alert at pump 10, a remote location or both alerting the patient or clinician that a short circuit condition has likely occurred and to check cord 102, as seen at block 172. A failed confirm can stem from the confirm request signal not reaching the remote controller 112 or from the remote controller 112 receiving the request but not being able to respond to the local controller 110.

If a confirm signal is sent back from remote controller 112 to local controller 110, as determined at diamond 168, the local integrated circuit sends a "provide bolus" signal or output to actuator processing an memory 108, as seen at block 174, which causes the pump actuator to provide a bolus of analgesic to the patient as seen at block 176. Thus, if after a bolus request, the two controllers 110 and 112 are able to communicate, the request is seen as a legitimate request from the patient instead of a short circuit between wires of cords. If after the bolus request, however, the two controllers 110 and 112 are not able to communicate, the request is seen as stemming from some sort of short circuit between the wires of cord 102 that have inadvertently caused a bolus request signal to be sent. Algorithm 160 then ends as seen at oval 178.

Figure 9:
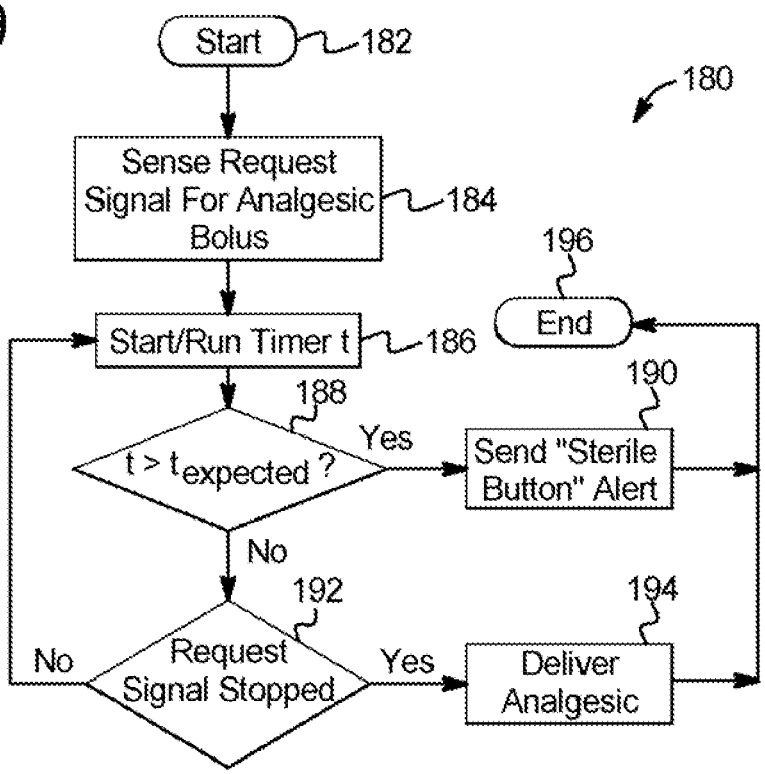
FIG. 9 is a logic flow diagram illustrating one stuck button method of operation for the PCA apparatus of the present disclosure.

Referring now to FIG. 9, an algorithm 180 stored at any of local controller 110, remote controller 112 and actuator processing and memory 108 illustrates one embodiment in which the PCA system of the present disclosure is configured to determine when button 104 of PCA input device 100 has become stuck. In one embodiment, button 104 is a momentary pushbutton which only has to make an electrical contact for a short period of time for remote controller 112 to sense an input from the patient and send a bolus request signal. Here, button 104 includes a spring that unmakes electrical contact when the patient removes his or her thumb or finger from button 104. Momentary button 104 can become stuck such that the electrical contact is not un-maid when the patient releases from button 104.

Algorithm 180 starts at oval 182 when the patient presses button 104 and a request for analgesic bolus is sensed at block 184. Upon sensing the request signal, algorithm 180 starts a timer "t" at block 186. If timed "t" is greater than an expected time $t_{expected}$ as determined at diamond 188, a "stuck button" alert is provided, which can be an audio, visual or audiovisual alert at pump 10, a remote location or both, which alerts the patient or clinician that a stuck button condition has likely occurred, as seen at block 190.

If however timed "t" is not greater than an expected time $t_{expected}$ as determined at diamond 188, algorithm 180 determines if the bolus request signal has stopped as determined at diamond 192. If the timer signal has not stopped, timing continues at block 186 and the loop of block 186, diamond 188 and diamond 192 continues until timed "t" is greater than an expected time $t_{expected}$ (diamond 188) or the request signal stops (diamond 192).

If the request signal stops as determined at diamond 192 before timed "t" reaches $t_{expected}$, the bolus of analgesic is delivered to the patient as seen at block 194. Here, the momentary signal stops before a stuck or sticking bolus button 104 is detected. Upon sounding the alert or providing the analgesic bolus, algorithm 180 ends as seen at oval 196.

Figure 10:
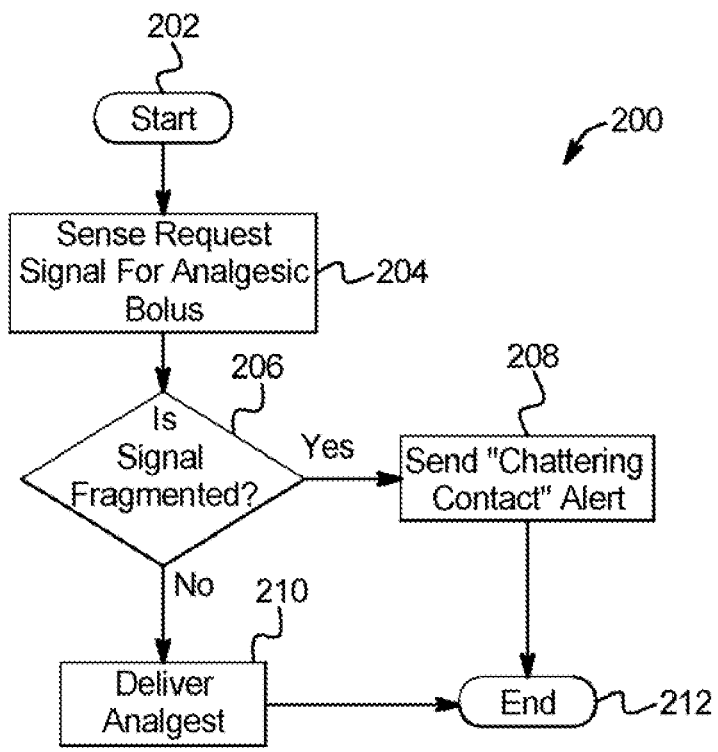
FIG. 10 is a logic flow diagram illustrating one chattering contact method of operation for the PCA apparatus of the present disclosure.

Referring now to FIG. 10, an algorithm 200 stored at any of local controller 110, remote controller 112 and actuator processing and memory 108 illustrates one embodiment in which the PCA system of the present disclosure is configured to determine when button 104 of PCA input device 100 has a chattering contact. In one embodiment, button 104 is a maintained pushbutton, which when pressed stays depressed until another event occurs, e.g., another button is pressed or a timer times out. Maintained button 104 when depressed can have a contact that chatters back and forth instead of making steady contact.

Algorithm 200 starts at oval 202 when the patient presses button 104 and a request for analgesic bolus is sensed at block 204. If the signal sensed is fragmented or not continuous, as determined at diamond 206, a "chattering contact" alert is provided, which can be an audio, visual or audiovisual alert at pump 10, a remote location or both, which alerts the patient or clinician that the button 104 is not functioning properly, as seen at block 208. If however the request signal is continuous or non-fragmented, as determined at diamond 206, the bolus of analgesic is delivered to the patient as seen at block 210. Upon sounding the alert or providing the analgesic bolus, algorithm 200 ends as seen at oval 212.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An infusion pump comprising:
a housing;
a pump actuator supported by the housing;
electronics configured to control the pump actuator;
a pain controlled analgesic ("PCA") input device;
a cord having a remote end connected to the PCA input device and a local end connected to the housing;
a remote integrated circuit; and
a local integrated circuit in communication with the electronics and the remote integrated circuit so as to provide operational information concerning the PCA input device to the electronics, wherein the local integrated circuit is located within the cord at the local end and the remote integrated circuit is located within the cord at the remote end.

2. The infusion pump of claim 1, wherein the electronics are configured to control the pump actuator includes programmable processing and memory.

3. The infusion pump of claim 1, wherein the PCA input device includes at least one button.

4. The infusion pump of claim 1, wherein the remote integrated circuit is in communication with the local integrated circuit via a protocol selected from the group consisting of: Inter-Integrated Circuit ("I²C"), Serial Peripheral Interface Bus ("SPI"), Transistor-Transistor Logic Universal Asynchronous Receiver/Transmitter ("TTL UART"); RS 232 Universal Asynchronous Receiver/Transmitter ("RS232 UART"), and fiber optics.

5. The infusion pump of claim 1, wherein the operational information concerning the PCA input device includes a request from the remote integrated circuit for a bolus of analgesic.

6. The infusion pump of claim 5, wherein the remote integrated circuit is configured to send the bolus request upon receiving an input from the PCA input device by a patient.

7. The infusion pump of claim 5, wherein one of the (i) local integrated circuit and (ii) the electronics is configured to apply at least one rule to determine if the bolus of analgesic should be delivered.

8. The infusion pump of claim 7, wherein the at least one rule includes whether the bolus request has occurred too soon after a previous bolus of analgesic delivery.

9. The infusion pump of claim 1, wherein the operational information concerning the PCA input device includes whether the remote and local integrated circuits can communicate.

10. The infusion pump of claim 1, wherein the operational information concerning the PCA input device includes whether the PCA input device is functioning properly.

11. The infusion pump of claim 10, wherein the information concerning whether the PCA input device is functioning properly includes at least one of: (i) information concerning a button of the PCA input device being stuck and (ii) information concerning a switch closure of the PCA input device operating improperly.

12. An infusion pump comprising:
a housing;
a pump actuator supported by the housing;
electronics configured to control the pump actuator;
a pain controlled analgesic ("PCA") input device;
a cord having a first end and a second end, the cord connecting the PCA input device to the housing;

a first integrated circuit; and a second integrated circuit in communication with the first integrated circuit, at least one of the first and second integrated circuits in communication with the electronics, the first and second integrated circuits configured and arranged with respect to the PCA input device and the housing to detect whether the PCA input device is functioning properly, wherein the first integrated circuit is located within the cord at the first end and the second integrated circuit is located within the cord at the second end.

13. The infusion pump of claim 12, the first integrated circuit associated with the PCA input device, and wherein being configured to detect whether the PCA input device is functioning properly includes being configured to determine if the first integrated circuit can communicate with (i) the electronics or (ii) the second integrated circuit.

14. The infusion pump of claim 12, wherein being configured to detect whether the PCA input device is functioning properly includes being configured to determine if a button of the PCA input device is stuck.

15. The infusion pump of claim 12, wherein being configured to detect whether the PCA input device is functioning properly includes being configured to determine if a switch contact of the PCA input device is functioning properly.

16. An infusion pump comprising:
a housing;
a pump actuator supported by the housing;
electronics configured to control the pump actuator;
a pain controlled analgesic ("PCA") input device;
a cord connecting the PCA input device and the housing; and
first and second integrated circuits positioned within the cord and configured to determine at least one of: (i) integrity of wiring within the cord; and (ii) integrity of the PCA input device, wherein the first integrated circuit is located within the cord at a first end and the second integrated circuit is located within the cord at a second end.

17. An infusion pump comprising:
a housing;
a pump actuator supported by the housing;
electronics configured to control the pump actuator;
a pain controlled analgesic ("PCA") input device;
a cord having a remote end connected to the PCA input device and a local end connected to the housing;
a remote integrated circuit; and
a local integrated circuit in communication with the electronics and the remote integrated circuit so as to provide operational information concerning whether the PCA input device is functioning properly to the electronics, wherein at least one of the local integrated circuit and the remote integrated circuit is located within the cord, and wherein the operational information includes at least one of: (i) information concerning a button of the PCA input device being stuck and (ii) information concerning a switch closure of the PCA input device operating improperly.

18. The infusion pump of claim 17, wherein the electronics are configured to control the pump actuator includes programmable processing and memory.

19. The infusion pump of claim 17, wherein the remote integrated circuit is located within the cord at the remote end and the local integrated circuit is located within the cord at the local end.

20. The infusion pump of claim 17, wherein the remote integrated circuit is located within the cord at the remote end.

21. The infusion pump of claim 17, wherein the local integrated circuit is located within the cord at the local end.

22. The infusion pump of claim 17, wherein the remote integrated circuit is in communication with the local integrated circuit via a protocol selected from the group consisting of: Inter-Integrated Circuit ("I$^2$C"), Serial Peripheral Interface Bus ("SPI"), Transistor-Transistor Logic Universal Asynchronous Receiver/Transmitter ("TTL UART"); RS 232 Universal Asynchronous Receiver/Transmitter ("RS232 UART"), and fiber optics.

23. The infusion pump of claim 17, wherein the operational information concerning the PCA input device includes a request from the remote integrated circuit for a bolus of analgesic.

24. The infusion pump of claim 23, wherein the remote integrated circuit is configured to send the bolus request upon receiving an input from the PCA input device by a patient.

25. The infusion pump of claim 23, wherein one of the (i) local integrated circuit and (ii) the electronics is configured to apply at least one rule to determine if the bolus of analgesic should be delivered.

26. The infusion pump of claim 25, wherein the at least one rule includes whether the bolus request has occurred too soon after a previous bolus of analgesic delivery.

27. The infusion pump of claim 17, wherein the operational information concerning the PCA input device includes whether the remote and local integrated circuits can communicate.

28. An infusion pump comprising:
a housing;
a pump actuator supported by the housing;
electronics configured to control the pump actuator;
a pain controlled analgesic ("PCA") input device;
a first integrated circuit; and
a second integrated circuit in communication with the first integrated circuit, at least one of the first and second integrated circuits in communication with the electronics, the first and second integrated circuits configured and arranged with respect to the PCA input device and the housing to detect whether the PCA input device is functioning properly and provide operational information concerning the PCA input device to the electronics including at least one of: (i) information concerning a button of the PCA input device being stuck and (ii) information concerning a switch closure of the PCA input device operating improperly.

29. The infusion pump of claim 28, the first integrated circuit associated with the PCA input device, and wherein being configured to detect whether the PCA input device is functioning properly includes being configured to determine if the first integrated circuit can communicate with (i) the electronics or (ii) the second integrated circuit.

30. The infusion pump of claim 28, wherein being configured to detect whether the PCA input device is functioning properly includes being configured to determine if a switch contact of the PCA input device is functioning properly.

31. The infusion pump of claim 28, which includes a cord connecting the PCA input device to the housing.

32. The infusion pump of claim 31, wherein at least one of: (i) the first integrated circuit is located in the PCA input device or at a PCA input device end of the cord and (ii) the second integrated circuit is located in the housing or at a housing end of the cord.

33. The infusion pump of claim 31, wherein at least one of the first integrated circuit and the second integrated circuit is located within the cord.

34. An infusion pump comprising:
a housing;
a pump actuator supported by the housing;
electronics configured to control the pump actuator;
a pain controlled analgesic ("PCA") input device;
a cord connecting the PCA input device and the housing; and
first and second integrated circuits positioned with respect to the cord and configured to:
  determine at least one of: (i) integrity of wiring within the cord; and (ii) integrity of the PCA input device, and
  provide operational information concerning the PCA input device to the electronics including at least one of: (i) information concerning a button of the PCA input device being stuck and (ii) information concerning a switch closure of the PCA input device operating improperly.

35. The infusion pump of claim 34, wherein at least one of the first and second integrated circuits is located within the cord.

* * * * *